(12) United States Patent
Ostrovsky et al.

(10) Patent No.: US 9,623,265 B2
(45) Date of Patent: Apr. 18, 2017

(54) DEVICE FOR CONTROLLED TISSUE TREATMENT

(75) Inventors: Isaac Ostrovsky, Wellesley, MA (US); Ty Fairneny, Brighton, MA (US); Victor Shukhat, Canton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1757 days.

(21) Appl. No.: 11/397,122

(22) Filed: Apr. 3, 2006

(65) Prior Publication Data

US 2006/0241530 A1   Oct. 26, 2006

Related U.S. Application Data

(60) Provisional application No. 60/669,106, filed on Apr. 7, 2005.

(51) Int. Cl.
*A61N 7/02* (2006.01)
*A61B 90/00* (2016.01)

(52) U.S. Cl.
CPC .......... *A61N 7/02* (2013.01); *A61B 2090/036* (2016.02); *A61N 7/022* (2013.01)

(58) Field of Classification Search
CPC ..... A61B 2090/036; A61N 7/02; A61N 7/022
USPC .......................................... 601/2–3; 600/448
See application file for complete search history.

(56) References Cited

U.S. PATENT DOCUMENTS

| | | | |
|---|---|---|---|
| 4,277,711 A * | 7/1981 | Hanafy ......................... | 310/334 |
| 4,384,228 A * | 5/1983 | Dias ......................... | 310/313 D |
| 4,434,799 A * | 3/1984 | Taenzer ........................ | 600/448 |
| 4,556,070 A | 12/1985 | Vaguine et al. | |
| 4,938,217 A * | 7/1990 | Lele ................................. | 601/3 |
| 5,053,713 A * | 10/1991 | Henoch ......................... | 324/537 |
| 5,191,560 A | 3/1993 | Lobentanzer et al. | |
| 5,524,625 A | 6/1996 | Okazaki et al. | |
| 5,704,791 A * | 1/1998 | Gillio ............................. | 434/262 |
| 5,803,083 A * | 9/1998 | Buck et al. .................... | 600/439 |
| 5,873,845 A * | 2/1999 | Cline et al. ...................... | 601/3 |
| 6,190,353 B1 * | 2/2001 | Makower et al. ......... | 604/95.01 |
| 6,314,311 B1 * | 11/2001 | Williams et al. ............. | 600/425 |

(Continued)

FOREIGN PATENT DOCUMENTS

| | | |
|---|---|---|
| JP | 02-252449 | 10/1990 |
| JP | 5-137733 | 6/1993 |

(Continued)

*Primary Examiner* — Ruth S Smith
(74) *Attorney, Agent, or Firm* — Brake Hughes Bellermann LLP (57) ABSTRACT

A device for heating target tissue comprises a housing, an array of ultrasound transducers and a deflector member. The housing includes a tissue contacting surface. The array of ultrasound transducers is mounted within the housing on an array surface shaped so that ultrasound energy from the transducers converges on a target area a predetermined depth from the tissue contacting surface. The deflector member is located at a selected position within a field through which a portion of the ultrasound energy generated will pass on its way to the target area. The deflector member refracts a selected portion of the ultrasound energy to control a distance of separation between the array and a proximal edge of a region at which a level of ultrasound energy exceeds a predetermined threshold level.

15 Claims, 5 Drawing Sheets

(56) References Cited

U.S. PATENT DOCUMENTS

| | | |
|---|---|---|
| 7,033,328 B2 * | 4/2006 | Matula et al. ............... 601/2 |
| 2003/0113540 A1 * | 6/2003 | Anderson et al. ........... 428/403 |
| 2004/0015106 A1 | 1/2004 | Coleman |
| 2006/0004306 A1 * | 1/2006 | Altshuler et al. ............ 601/3 |
| 2007/0073098 A1 * | 3/2007 | Lenker et al. ............... 600/30 |

FOREIGN PATENT DOCUMENTS

| | | |
|---|---|---|
| JP | 5-309099 | 11/1993 |
| JP | 07-178109 | 7/1995 |
| JP | 2004130145 | 4/2004 |

* cited by examiner

DEVICE FOR CONTROLLED TISSUE TREATMENT

PRIORITY CLAIM

The present invention claims the benefit of U.S. Provisional Patent Application No. 60/669,106 entitled "Apparatus and Method for Controlled Tissue Treatment" filed Apr. 7, 2005, the entire disclosure of which is expressly incorporated herein by reference.

FIELD OF THE INVENTION

The present invention generally relates to medical devices and tissue treatment methods. Specifically, the present invention relates to devices and methods for providing energy to target tissue. More particularly, the present invention describes an apparatus and method to treat urinary incontinence and, more particularly, stress incontinence with a vaginal probe.

BACKGROUND

Stress urinary incontinence (SUI) occurs when tissue supporting the pelvic floor no longer provides sufficient support to the bladder neck and urethra, particularly the proximal urethra. Because of this condition, the bladder pushes against the urethra. Pressure from the abdominal muscles (e.g. during such activities as laughing, sneezing, coughing, exercising or straining to lift objects) can then cause undesired urine emissions. Females whose pelvic floors have stretched due to, for example, childbirth, obesity, etc. are more likely to suffer from stress incontinence.

Several treatments for SUI are available, ranging from medications to surgical interventions. One minimally invasive treatment for SUI utilizes radio frequency (RF) energy delivered to tissue of the pelvic floor, specifically to the endopelvic fascia (EPF) which lies beneath the surface of the vaginal wall. The RF energy heats the tissue of the endopelvic fascia and causes the collagen in the tissue to denature, so that the fascia shrinks. When the fascia shrinks, it returns the bladder and urethra to a more natural position within the pelvis, reducing the symptoms of incontinence. Other types of energy may be used to heat the tissue, such as acoustic energy, laser energy, microwaves etc.

Procedures to treat the endopelvic fascia require the accurate placement of the energy source within the vaginal canal of the patient, to successfully heat the target tissue. More generally, there are many medical procedures where a probe or other 'medical implement is inserted into a body lumen or cavity, to achieve some therapeutic effect on the surrounding tissue. In all these procedures, it is important to be able to accurately place the probe or other device relative to the target tissue, without direct visualization of the device. This task may be made difficult because of the geometry of the lumen, or because of the lack of convenient reference points near the opening of the lumen.

SUMMARY OF THE INVENTION

In one aspect, the present invention is directed to a device for heating target tissue comprising a housing, an array of ultrasound transducers and a deflector member. The housing includes a tissue contacting surface. The array of ultrasound transducers is mounted within the housing on an array surface shaped so that ultrasound energy from the transducers converges on a target area a predetermined depth from the tissue contacting surface. The deflector member is located at a selected position within a field through which a portion of the ultrasound energy generated will pass on its way to the target area. The deflector member refracts a selected portion of the ultrasound energy to control a distance of separation between the array and a proximal edge of a region at which a level of ultrasound energy exceeds a predetermined threshold level.

BRIEF DESCRIPTION OF DRAWINGS

FIG. 2b shows a profile of ultrasound energy administered by the apparatus of FIG. 2a;

FIG. 3b shows a profile of ultrasound energy administered by the apparatus of FIG. 3a;

DETAILED DESCRIPTION

The present invention may be further understood with reference to the following description and the appended drawings, wherein like elements are referred to with the same reference numerals. The present invention is related to medical devices used to treat tissue adjacent to the walls of a body lumen or cavity, and to determine the position of the devices within the lumen. More specifically, the invention relates to a system for determining the position, relative to the urethra, of a device inserted into the vaginal canal for treatment of the endopelvic fascia.

Many medical procedures rely on inserting a medical implement into a body cavity or lumen of a patient, to carry out some therapeutic activity. For example, energy may be delivered from a probe into tissue surrounding the body cavity or lumen, to heat the tissue, to ablate portions of target tissue, or for other purposes. Energy may be delivered in the form of radio frequency energy, microwave energy, laser light, acoustic energy or any other appropriate form of energy. The location of the energy delivery probe within the lumen, in most cases, needs to be known so that the energy is delivered to the correct location to achieve the desired result. Direct visualization of the device, for example using fluoroscopy, may be used, however a simpler and less expensive way of determining the location of the device is often desirable.

One exemplary condition that can be alleviated by targeted delivery of energy is stress urinary incontinence (SUI). The treatment of SUI by altering the properties of the endopelvic fascia adjacent to the anterior vaginal wall and to the urethra is enhanced when the location on the endopelvic fascia of the tissue to be treated is precisely determined, and when treatment is accurately delivered to this location.

Figure 1A:
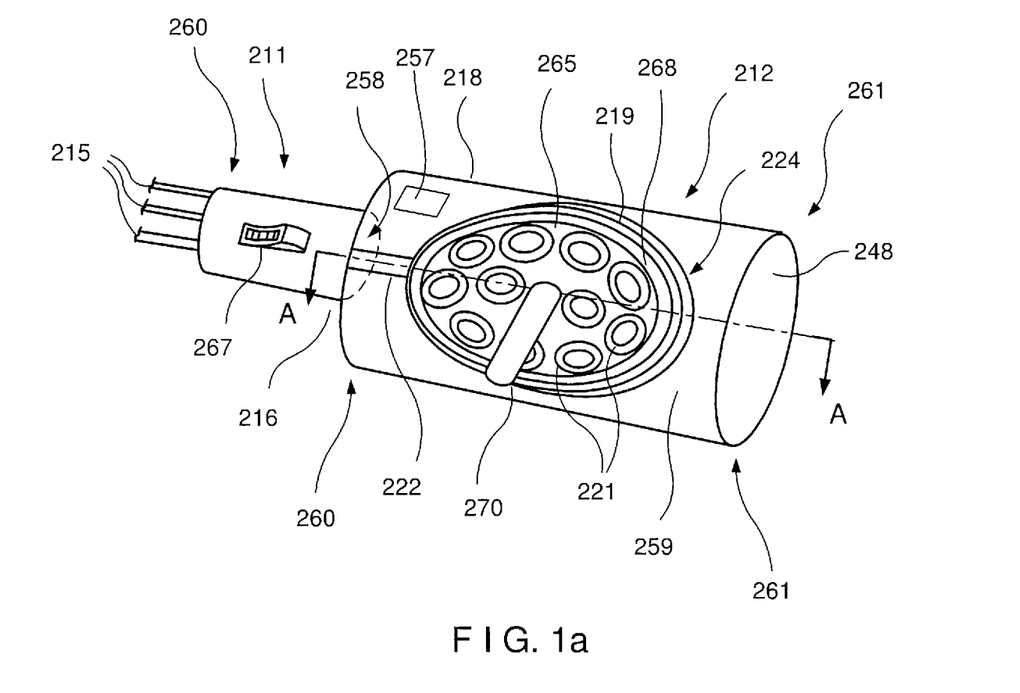
FIG. 1a shows an exemplary embodiment of an apparatus for administering ultrasound energy to tissue according to the present invention.

An exemplary embodiment of the medical device according to the present invention is shown in FIG. 1a. In this embodiment, the apparatus may comprise a handle 211 which can be manipulated by a user and an operative probe 212 which is insertable into the body via a naturally occurring orifice (e.g., vagina, mouth, anus, etc.) or a non-naturally occurring orifice (e.g., incision, wound, etc.). Thus, during a medical procedure, the probe 212 may be disposed adjacent or substantially adjacent to any tissue within the body.

The probe 212 extends from a proximal end 260 to a distal end 261, with a probe cavity 259 formed therein. The probe cavity 259 may be formed in any size and/or shape compatible with the anatomical structures to be treated via insertion of the probe 212. The probe 212 preferably comprises a casing 218 enclosing the probe cavity 259 and an ultrasound element 219 disposed therein. The casing 218 may have any desired shape compatible with the anatomy for which the probe 212 is utilized. In one embodiment, the shape of the casing 218 is formed so that a shape of a portion of the outer surface of the casing 218 through which energy will pass from the ultrasound element 219 to the target tissue couples to the tissue surface which it will be contacting (e.g., as a shape of the casing conforms to that of the tissue or vice versa). That is, since ultrasound energy emitted by the ultrasound element 219 passes more efficiently when there are no air gaps between the ultrasound element 219 and the target tissue, the casing 218 may be shaped to ensure that direct contact with an intervening tissue surface may be easily maintained. For example, depending on the area of treatment, the casing 218 may be substantially cylindrical or may include a substantially planar face or faces. The casing 218 is more preferably a sonolucent dome or membrane with a coupling medium filling the casing 218 and/or the probe cavity 259 allowing the ultrasound waves to propagate therethrough to the tissue. As would be understood by those skilled in the art, the coupling medium may be a liquid (e.g., water, degassed water, etc.), a gel, or any other desired medium, preferably with an acoustic impedance similar to that of water. Furthermore, if this medium is circulated, it will also assist in removing heat from the tissue in immediate contact with the casing 218. Further, this medium or any other material suitable for use as the coupling medium may also be applied to an outer surface of the casing 218 to reduce the chances of infection.

In one embodiment, the probe 212 is preferably manufactured from low-cost materials so that it may be employed as, for example, a single-use, disposable item. In a further embodiment, the probe 212 may be a re-usable item which is sterilized before and after use. As would be understood by those skilled in the art, the size and shape of the probe 212 will be generally dictated by the anatomy with which it is to be used. For example, if the probe 212 is designed for use intra-vaginally, the probe 212 will preferably be no more than 6 to 7 cm long with a diameter of 1 to 4 cm. Of course, if the probe 212 is to be used during an invasive procedure the size may vary depending on the incision and/or method of accessing the target tissue within the body.

The handle 211 may have a control element 267 thereon, or the control element 267 may be located on a control device located near an operating or examining area. The control element 267 may be a switch, button, dial, foot pedal or any other desired mechanism that will allow the user to activate the probe 212. The size, shape and orientation of the handle 211 may be varied to achieve a desired feel or balance, but is preferably substantially tubular or ergonomically shaped for gripping by a user's hand. During a medical procedure, the user may grasp a portion of the handle 211 while a further portion of the handle 211 is within the body of the patient. For example, the further portion of the handle 211 may follow the probe 212 into the vagina as the probe 212 is advanced distally therein. In this embodiment, the control element 267 is preferably located on the portion of the handle 211 which is grasped by the user (e.g., outside the body) or at a remote location (e.g., the control device). Any suitable method of manufacturing, such as injection molding, machining, etc., may be used to construct the handle 211, from any suitable material (e.g. plastic, metal or combination thereof).

The handle 211 may include a handle lumen 258 allowing power and feedback cables 215 and any other elements (e.g., fluid lumens) to pass through the handle lumen 211 to the probe 212. The elements passing through the handle 211 may include, for example, a power supply and other electric cables to and from the ultrasound element 219, drive shafts and other members for rotating the probe 212 relative to the handle 211, fluid lumens, and/or any other elements contained therein. In one embodiment a distal end 216 of the handle 211 is connected to and opens into the probe 212. A diameter or cross-section of the handle 211 is preferably less than that of the probe 212 with the relative dimensions thereof depending upon the application, user-defined preferences, the target tissue to be treated and the anatomy of the organs or region of the body into which the device is to be introduced.

In the embodiment shown in FIG. 1a, the handle 211 and the probe 212 are fixedly coupled to one another in an axial alignment to reduce the arbitrariness of the waving of the apparatus by the user. In a separate embodiment (not shown) the handle 211 and the probe 212 may be rotatably and/or hingedly coupled to one another by a coupling mechanism so that an angle/position of the probe 212 relative to the handle 212 may be dynamically or incrementally varied to aid in properly positioning the probe 212 relative to the target tissue. That is, the angle/position may be varied to facilitate placement of the probe 212 flush against the desired tissue surface adjacent to the target tissue to maximize energy delivery to the target tissue. The probe 212 may be rotated about a longitudinal axis thereof to employ a sweeping motion over the target tissue or to reach further target tissues. As would be understood by those skilled in the art, the coupling mechanism may be a locking hinge or swivel or any other coupling mechanism means which allows for dynamic and/or incremental movement of the probe 212 relative to the handle 211. Use of the coupling mechanism contemplates movement of the probe 212 in any or all directions (i.e. laterally, vertically, axially and angularly) relative to the handle 211.

As would be understood by those skilled in the art, any or all of the apparatus, particularly the handle 211 and the casing 218 may be manufactured from any biocompatible material (e.g., polyethylene, polypropylene, etc.) showing the desired mechanical properties. Hence, these portions of or the entire apparatus may be employed as a single-use item and disposed of after use. Alternatively, the user may dispose of the probe 212 and/or the casing 218 after each use while the remaining components of the apparatus are conditioned and fitted with a new casing 218 for subsequent use.

As shown in FIG. 1a, an armature 222 extends through the handle 211 into the probe 212 where it is attached to the ultrasound element 219 within the casing 218. In one embodiment, a proximal end of the armature 222 is coupled to a displacement actuator (not shown) disposed on the proximal end of the handle 211 so that, movement and/or rotation of the displacement actuator relative to the handle 211 causes a corresponding movement of the armature 222 and, consequently, of the ultrasound element 219 relative to the casing 218. As would be understood by those skilled in the art, the displacement actuator may include one or more of a disc, gear, lever, or other element which allows the user to rotate the armature 222 relative to the handle 211 and/or to move the armature 222 axially relative to the handle 211 to alter a direction of transmission of the ultrasound energy from the ultrasound element 219. Alternatively, the armature 222 may be adapted electronically to rotate and/or move axially, for example, through a combination of control logic circuits and servo motors. As would be understood by those skilled in the art, mechanical and/or electronic control of the axial movement and rotation of the ultrasound element 219 allows the user to position the probe 212 so that the ultrasound energy 212 is accurately applied to the target tissue.

FIG. 1a shows one embodiment of the ultrasound element 219 according to the invention. In this embodiment, the ultrasound element 219 includes an array of ultrasound transducers 221 disposed on a partially spherical concave surface 265 of a base 224. Each of the transducers 221 includes one or more ultrasound crystals comprised of, for example, PZT (Lead Zirconate Titanate) or any other piezo-electric material. Each of the transducers 221 is bonded to a substantially rigid intermediate plate 268 which is preferably formed of a material such as copper which may be strongly bonded to the base 224 to prevent the crystal from shaking loose from the base 224 as it vibrates to generate the ultrasound energy. The intermediate plate 268 may be utilized for any shape, size or configuration of the transducers 221. Preferably, a thin layer of epoxy will be used to bond each of the transducers 221 to the intermediate plate 268 with an additional coat of epoxy applied to the intermediate plate 268 to bond it to the base 224. As would be understood by those skilled in the art, the epoxy may be replaced by another suitable adhesive compound or method, but preferably any compound used has an acoustic impedance similar to that of water. As would be understood by those skilled in the art, the number, size, shape and orientation of the transducers 221 in any of the described embodiments may be varied to deliver the desired energy pattern to the target tissue in the most efficient manner. For example, the transducers 221 may be oriented on a base with a surface that is concave, substantially planar, convex, etc. In addition, those skilled in the art will understand that the array of transducers 221 may be replaced by a single transducer having a shape similar to that of the array 221 so that a similar spot field for the generated energy is achieved, which will be described below. As would be understood by those skilled in the art, the ultrasound element 219 may either be fully enclosed in the casing 218 or may be exposed and in substantially the same plane as a surface of the casing 218. If the transducers 221 are in the same plane as the casing surface, rotation of the armature 222 will rotate the entire probe 212 of the apparatus.

For example, the apparatus may be used to create lesions and heat other target tissues at depths between about 0.5 and 3 cm below the tissue surface with which the casing 218 is in contact. If the transducers 221 are circular with a diameter (D) of approximately 1 cm, vibrating the transducers 221 at a frequency (F) of 2.5 MHz produces a beam of energy which remains collimated (i.e., substantially cylindrical) for approximately a length (L) of 4 cm before diverging (near field). As the velocity of sound is approximately 1,500 m/sec, the wavelength $\lambda$ is equal to 0.6 mm (1,500 m/sec*1/F) and the distance is calculated as: $L=D^2/4\lambda$. Thus, for a circular transducer 221 of 1 cm diameter, L equals approximately 4 cm. This is approximately the maximum effective converging distance for an ultrasound element 19 including transducers 221 of these diameters at F=2.5 MHz. If each ultrasound beam travels the entire distance through tissue, the maximum attenuation of the energy is 1 dB/MHz/cm*2.5 MHz*4 cm=10 dB. Thus, approximately one tenth of the original transducer power would remain at a convergence spot at the distance L. Thus, to achieve a greater power at the convergence spot than is generated by any individual transducer 221 at its surface, beams from more than 10 transducers would need to converge at the convergence spot.

As further shown in FIG. 1a, the ultrasound element 219 includes a beam deflector 270 projecting distally therefrom. In one exemplary embodiment shown in FIG. 1b, the deflector 270 is an elongated member including a distal end 274 and a proximal end 272 is attached to the base 224. In this embodiment and when the apparatus is disposable, the proximal end 272 may be bonded or welded to the base or formed integrally therewith. In another exemplary embodiment and when the apparatus is re-usable, the proximal end 272 may be threaded or configured in some other manner for temporary attachment to the base 224. For example, if the proximal end 272 is threaded, it may be received by a threaded bore in the base 224. The distal end 274 of the deflector 270 projects distally from the surface of the base 224. In any case, it is only necessary that the distal end 274 be located in the desired position relative to the base 224 and those skilled in the art will understand that the manner in which the distal end 274 is maintained in this location does not impact the functionality of the deflector 270.

Figure 1B:
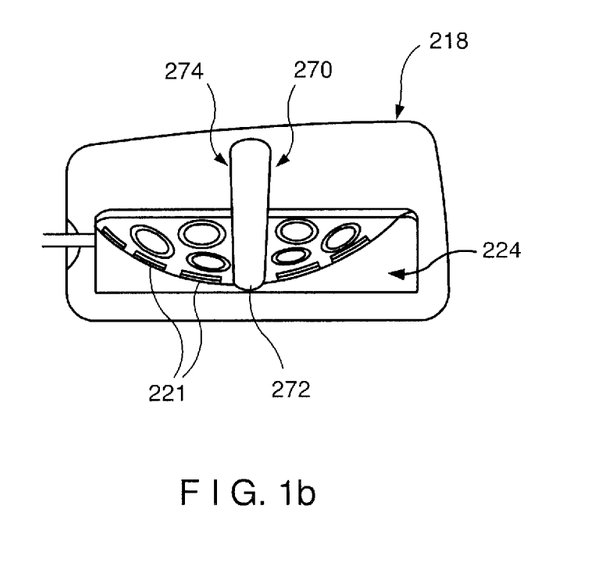
FIG. 1b shows a cross-section of the apparatus of FIG. 1a along the line A-A.

As shown in FIG. 1b, the deflector 270 may be cylindrical with a constant diameter along a predetermined length thereof. In one embodiment, the deflector 270 extends from a predetermined location on the base 224 which is preferably near a center thereof. For example, when the base 224 defines a substantially spherical concave surface on which the transducers 221 are located, the deflector 270 preferably extends substantially perpendicular to a tangent of the base 224 at that point. In this case, the deflector would be substantially perpendicular to the longitudinal axis of the probe 212. However, those of skill in the art would understand that the deflector 270 may be positioned anywhere on the base 224, and, if the ultrasound element 219 does not rotate within the base 224, the deflector 270 may be fixed to a predetermined location on the casing 218. Furthermore, it is preferred that the distal end 274 does not contact the casing 218 to prevent friction resulting from the distal end 274 contacting the casing 218 while the ultrasound element 219 is rotating. As understood by those of skill in the art, the deflector 270 may be of any size and/or shape, positioned anywhere on the base 224 and be manufactured from any suitable material, such as, for example, the same material used to manufacture the probe 212 and/or the handle 211.

Those skilled in the art will understand that the position, material and shape of the deflector 270 will be selected depending differences between the desired geometry of a lesion from the geometry of the convergence area that would result without a deflector. Thus, the deflector would be used to sculpt a desired lesion geometry and may be based on calculations, empirical methods or both. Those skilled in the art will further understand that Shlieren optics may be used to observe the ultrasound field in real time and make fine adjustments to the deflector position or other variables to obtain a desired lesion geometry.

Figure 2A:
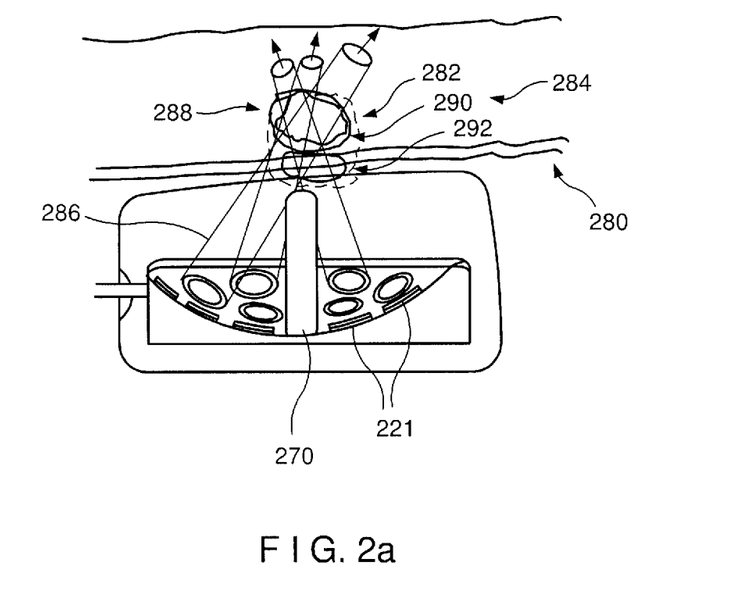
FIG. 2a shows the apparatus of FIG. 1 administering ultrasound energy to tissue.

In FIG. 2a, the apparatus is shown inserted to a position within the body adjacent to target tissue. The probe 212 is generally positioned with the casing 218 flush against the tissue surface 280 with the deflector 270 extending along an axis which, if extended, would pass through a target location at which a lesion 282 is to be created within tissue 284. For example, a longitudinal axis of the deflector 270 is preferably aligned with a center of the proposed lesion 282. As understood by those of skill in the art, different orientations of the deflector 270, the surface of the base 224 and the probe 212 relative to the handle 211 may require different positioning of the probe 212 relative to a desired location for the lesion 282.

When power is supplied to the probe 212 or when the probe 212 is activated using the control element 267, each transducer 221 generates ultrasound energy which propagates radially away from each transducer 221. The energy is mainly focused in beams 286 which converge at a field 288 separated by a predetermined distance from the ultrasound element 219. The intensity of ultrasound energy at the field 288 is directly proportional to a number of the transducers 221 in the ultrasound element 219. For example, the greater the number of transducers 221, the higher the intensity of the ultrasound energy.

Figure 2B:
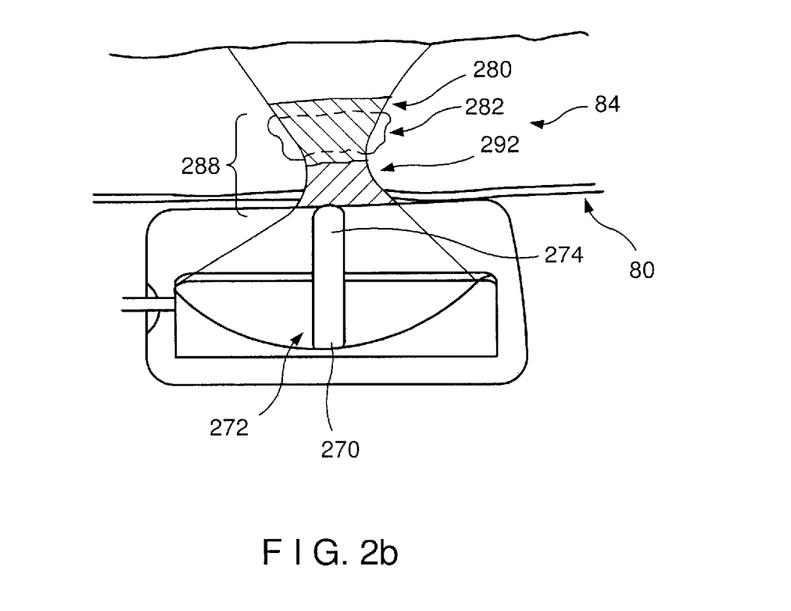

As shown schematically in FIG. 2b, a profile of a composite ultrasound beam comprised of the beams 286 from the transducers 221 has a diameter that is larger in the area directly adjacent to the transducers 221 and which decreases as the target area is approached. The composite ultrasound beam has a smaller diameter as it passes the distal end 274 of the deflector 270 and reaches a minimum diameter at the center of the field 288. Distally of this point, the individual beams 286 begin to diverge and the diameter of the composite beam increases with further movement distally. The area of convergence includes a necked portion indicated by the field 288, the shape of which is defined by the size and shape of the transducer 219, which in turn is restricted by the body cavity into which it is inserted. The area 288 represents an area of higher energy density within which maximum heating would occur. On another hand, the area to be treated with heat is limited by a specific application. For example, if it is not desired to treat the tissue surface, heat treatment must start further distally from the casing 218. The deflector 270 shadows a portion of the area (292), shortening the higher intensity area 288 to smaller size (290). The ratio of the shadowed vs. hot areas, or the diameter and the depth of the treated area are affected by the location, size and shape of the deflector 270. That is, interaction between the beams 286 from the transducers 221 and the deflector 270 creates energy characteristics unique to each of the areas 290 and 292 while a geometry of each may be relatively similar. In this embodiment, both the distal area 290 and the proximal area 292 of the field 288 have tapered-conical shapes, while one is inverted relative to the other. When a beam 286 is emitted from the transducer 221, a portion of the beam 286 (e.g., ultrasound waves) is refracted by the deflector 270 and does not reach the proximal area 292 of the field 288. As the bent portion of the beam 286 is not incident upon the convergence area in the field 288, the total ultrasound energy delivered to the proximal area 292 is reduced. Thus, by controlling the number of beams 286 which are bent by the deflector 270 away from the proximal area 292, the total ultrasound energy incident upon this proximal area 292 can be controlled to any value up to a maximum in which all of the beams reach the area 292. As understood by those of skill in the art, a centrally located deflector 270 will impact beams 286 originating from more centrally located transducers 221 more strongly when the deflector 270 is substantially circular. Thus, the shape of the deflector 270 and, more specifically, the size and shape of the distal end 274 may be controlled to select the transducers 221 whose beams 286 will be refracted away from the area 292. Those skilled in the art will understand that the pattern of the transducers 221 may be selected in combination with the shape of the distal end 274 such that some part of each radiated beam is deflected to create a lesion of a predetermined desired shape. Alternatively, a variety of effects including this one may be obtained by employing a control unit 257 to selectively disable various ones of the transducers 221 in a desired pattern or sequence to generate lesions of different sizes, shapes and locations. Furthermore, the transducer 219 may move or rotate relative to a deflector 270 of a non-circular shape which remains stationary or spins in the same direction at a different rate or spins in the opposite direction to selectively intercept energy from different ones of the transducers 221 to control the lesion characteristics. That is, for each beam 286, a first portion which is bent may not reach the proximal area 292 of the field 288, while a further portion remains unbent or is less bent as it passes by the distal end 274 without contacting the deflector 270 or slight contact with the deflector 270 does not deflect this portion of the ultrasound energy beyond the edge of the region 292. Thus, in one embodiment, the portion of each beam 286 which reaches the distal area 290 increases as a radial distance from the deflector 270 increases.

As noted above, without the deflector 270, the beams 286 would be incident on and converge on the entire field 288 including both the proximal and distal areas 290 and 292. However, as described above and as shown in FIG. 2b, the proximal area 292 may include non-targeted tissue such as surface tissue. According to the exemplary embodiment of the present invention, the deflector 270 creates a shadow area which substantially reduces ultrasonic energy reaching the proximal area 292 of the field 288. Thus, even where substantial energy is applied to tissue in the area 290, tissue in this proximal area 292 receives minimal energy and is unharmed. The geometry of each of the proximal area 292 and the distal area 290 may change as a result of, for example, a shape of the base 224, an alignment/configuration of the transducers 221, a radiation frequency, a level of power supplied to the transducers 221 and the size, shape and location of the deflector 270.

Ultrasonic energy applied to the distal area 290 is preferably at a predetermined level similar to that applied by an ultrasound element 219 without the deflector 270 so that this energy will be sufficient to create the lesion 282. Those of skill in the art will understand that the field 288, and thus the distal area 290, may have various locations relative to the probe 212, and those locations will depend on factors including, but not limited to, a shape of the base 224, an alignment/configuration of the transducers 221, a radiation frequency, a level of power supplied to the transducers 221 and the size, shape and location of the deflector 270.

Figure 3A:
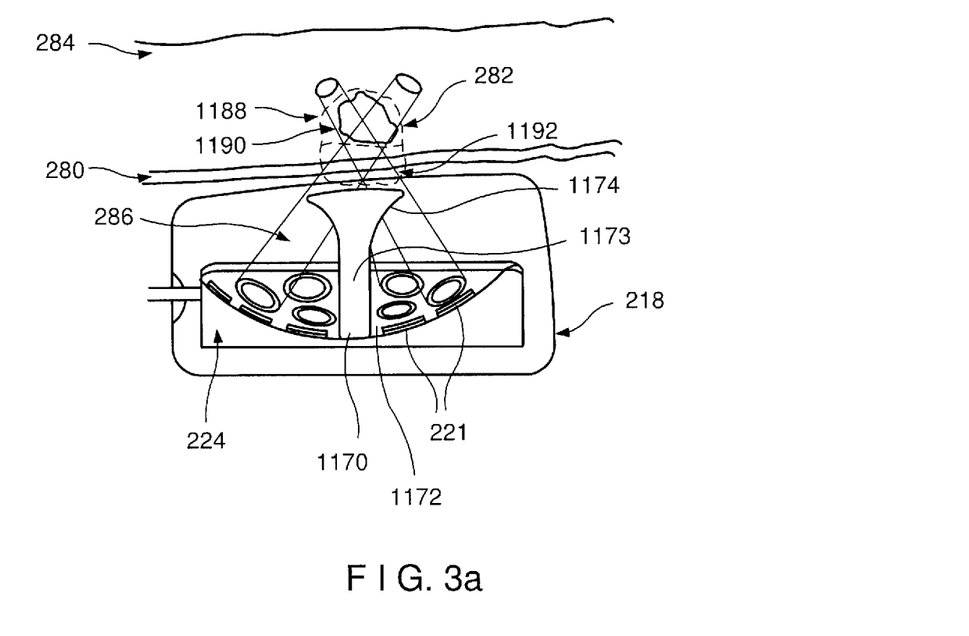
FIG. 3a shows another exemplary embodiment of an apparatus for administering ultrasound energy to tissue according to the present invention.

A further exemplary embodiment of a deflector 1170 according to the present invention is shown in FIG. 3a. In this embodiment, the deflector 1170 includes a proximal end 1172 maintained in position in any manner as described above with reference to the deflector 270. From the proximal end 1172, the deflector 1170 extends distally along a predetermined length reaching a transition zone 1173 and terminating at a distal end 1174. Between the proximal end 1172 and the transition zone 1173, the deflector 1170 is substantially cylindrical with a predetermined diameter along a first portion of its length. Extending distally from the transition zone 1173, the diameter may increase gradually, incrementally or abruptly. For example, in one embodiment, the transition zone 1173 is a conical or frusto-conical section along which a diameter increases gradually distally therealong. In another embodiment, the proximal end 1172 has a first diameter which increases abruptly to a second diameter to form a substantially disc-shaped distal end 1174. In yet another embodiment, there is no transition zone 1173, and the deflector 1170 is simply an elongated member attached to the base 224 at the proximal end 1172 with a plate at the distal end 1174. Those of skill in the art will understand that the elongated member and the plate may have any size, shape and/or configuration.

In this embodiment, a diameter of the distal end 1174 is larger than that of the proximal end 1172. In comparing FIGS. 2a and 3a, one of skill in the art will understand that this embodiment of the distal end 1174 will bend a greater portion and/or more of the beams 286 emitted from the transducers 221 than would the deflector 1170 without the increased diameter distal end 1174. The deflector 1170 also creates a spot field 1188 including a distal area 1190 and a proximal area 1192 each having a different geometry from those shown in FIGS. 2a and 2b. Those of skill in the art will understand that any desirable geometry for the spot field 1188 may be created by the manipulating a construction of the deflector 1170. The geometry may depend the number and location of the transducers 221 and on any of the above-noted factors, as well as, size, shape, composition and desired location of the lesion 282. For example, as the size of the desired lesion 282 increases, a radial dimension of the distal end 1174 of the deflector 1170 may be decreased to allow more beams 286, and thus more ultrasonic energy, to be incident upon the lesion 282. For example, if the desired lesion 282 is close to the tissue surface 280, a smaller distal end 1174 may be utilized to decrease the size of the shadow area by reducing the number of beams 286 which will be refracted by the deflector 1170 increasing the amount of energy incident upon the proximal area 1192.

Figure 3B:
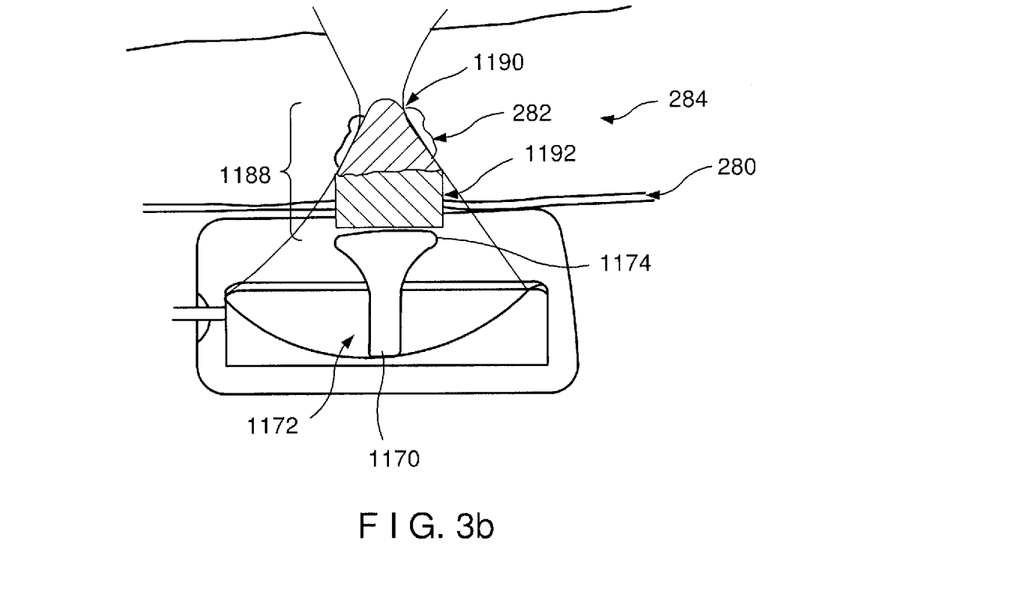

As shown schematically in FIG. 3b, a further composite ultrasound beam comprised of each of the beams 286 from the transducers 221 has a convergence field 1188 at a predetermined distance from the distal end 1174 of the deflector 1170. In this embodiment, the distal area 1190 is substantially conical, while the proximal area 1192 is substantially disc-shaped. As compared to the embodiment of FIGS. 2a and 2b, a greater portion of the beams 286 (e.g., ultrasound waves) from the transducers 221 are bent by the distal end 1174 of the deflector 1170 preventing this energy from reaching the proximal area 1192 of the field 1188. As a result, the level of ultrasonic energy in the proximal area 1192 is reduced and a proximal edge of the lesion 282 deeper in the tissue, e.g., the lesion is created in the distal area 1190 with little or no lesion formation in the proximal area 1192.

Figure 4:
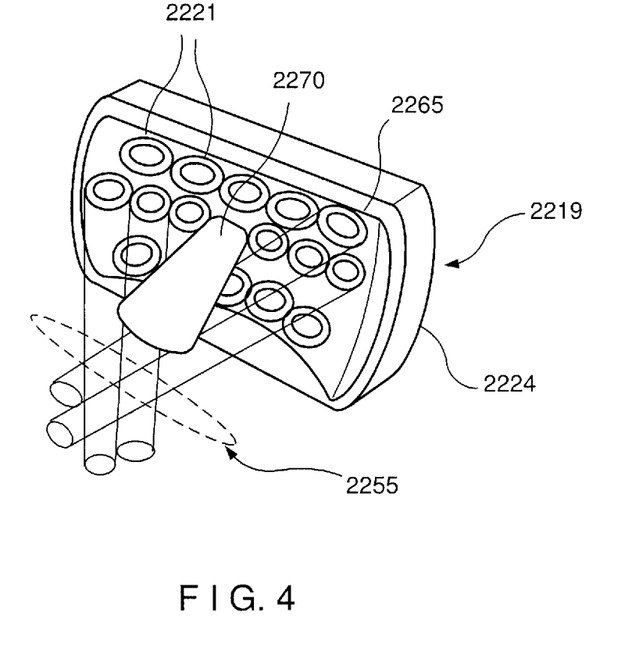
FIG. 4 shows a further exemplary embodiment of an apparatus for administering ultrasound energy to tissue according to the present invention.

FIG. 4 shows another exemplary embodiment of an ultrasound element 2219. In this embodiment, a base 2224 includes an array of transducers 2221 disposed on a surface 2265 that is concave and substantially ellipsoidal. As would be understood by those skilled in the art, the transducers 2221 may be arranged in a single line or in multiple lines in either a longitudinal or a transverse orientation, or in any other orientation or grouping as desired. The ultrasound element 2219 of this embodiment is concave in the form of a partially ellipsoidal bowl creating a substantially elliptical spot field 2255 at a predefined distance from the element 2219. As would be understood by those skilled in the art, any of the various ultrasound elements 219, 2219 may be employed with any of the various casings 218 and coverings described herein. The ultrasound element 2219 includes a deflector 2270 which may be constructed and positioned as a function of the dimensions and shape of the ultrasound element 2219 and its components as described in regard to any of the above embodiments.

As described above, when the target tissue is at a depth which approaches a maximum depth of energy penetration (based on the transducer dimensions and radiation frequency) before the energy dissipates, it is necessary to converge beams from more crystals on a spot to account for attenuation of the energy. Specifically, in the example given above, for a target depth of 4 cm with transducers 21 of D=1 cm and F=2.5 MHz, it is necessary to converge beams from more than 10 transducers 221 on the field to achieve greater power delivery at the field than is generated by each transducer. For example, in this embodiment, energy from 213 crystals converge on the field 2255 bringing approximately 1.3 times the energy to this spot as is generated by any one transducer. Those skilled in the art will understand that the surface 265 in the example of FIGS. 1a-3b may be a sphere of approximately 4 cm diameter to achieve this depth of convergence and that the surface 2265 of the apparatus of FIG. 4 may be an ellipsoid with a convergence area approximately 4 cm from the end thereof.

Figure 5:
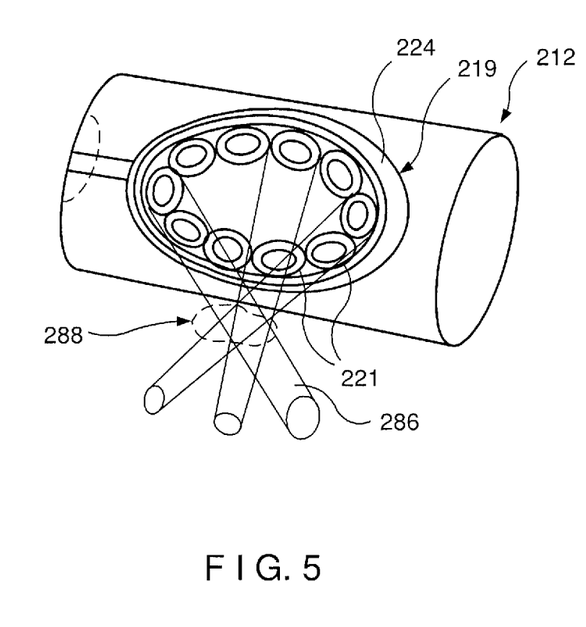
FIG. 5 shows yet a further exemplary embodiment of an apparatus for administering ultrasound energy to tissue according to the present invention.

FIG. 5 shows a further embodiment of the apparatus according to the present invention. In this embodiment, the transducers 221 are disposed on the spherical, concave surface of the base 224 and arranged in an annular orientation at a predetermined radial distance from the center of the ultrasound element 219. Thus, each transducer 221 emits a beam 286 of ultrasonic energy when the apparatus is activated, and the beam 286 is focused, unbent, on the target tissue. In this configuration, the field 288 of the generated by the beams 286 is substantially similar to that created by the embodiments of FIGS. 1a and 2a. However, the field 288 is generated at a predetermined distance beneath a surface of the tissue 284 due to the configuration of the transducers 221 rather than the deflector 270. In this embodiment, the field 288 does not include a proximal area.

Figure 6:
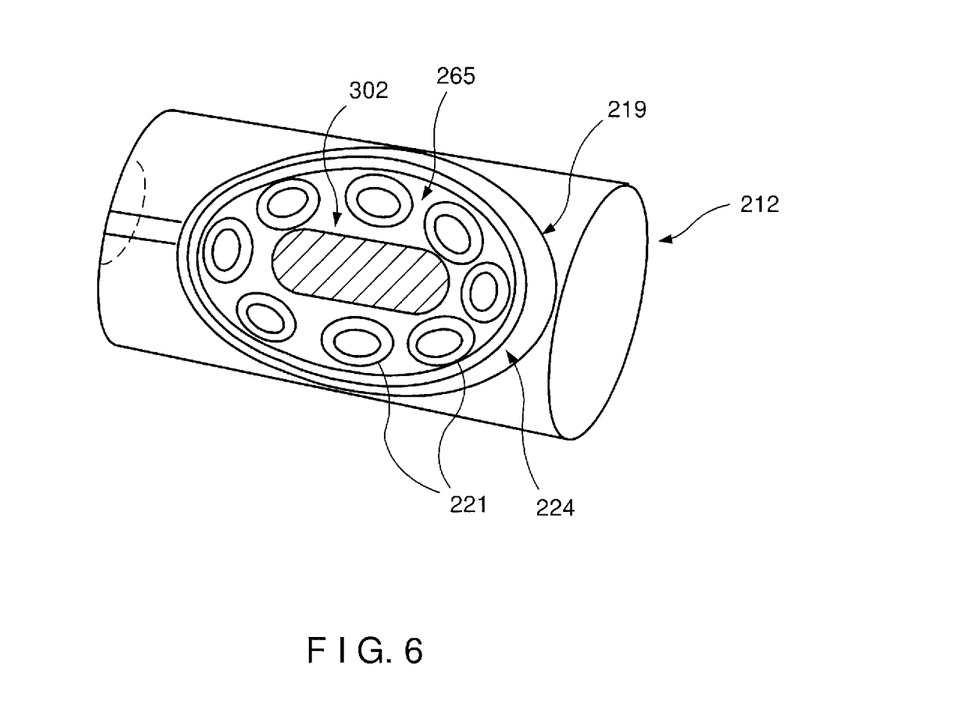
FIG. 6 shows another exemplary embodiment of an apparatus for administering ultrasound energy to tissue according to the present invention.

As shown in FIG. 6, in yet a further embodiment, preferably when the apparatus is re-usable, the transducers may be oriented as in FIG. 1a without the presence of the deflector 270. In this manner, activating the transducers 221 may produce heating effects at the lesion 282, as well as other portions and the surface of the tissue, which may be undesirable. Thus, a deflective sticker 302 may be placed over at least a portion of one or more of the transducers 221 to block or bend a portion of the beam 286 emitted therefrom to tailor a desired spot field 288 at a selected depth beneath the tissue surface 280. As would be understood by those skilled in the art, the sticker 302 may have a coating of adhesive allowing it to temporarily bond to the surface 265 without damaging the transducer(s) 221 therebelow.

The method according to the present invention will be described as creating a lesion, though the method may be used for the treatment of other conditions where the reshaping, stiffening and/or ablation of tissue (e.g., collagenous tissue) may be therapeutic. In a non-invasive procedure, the apparatus may be inserted into the body via a naturally occurring body orifice, such as, the vagina until the probe 12 contacts the vaginal mucosa, because the casing 18 and coupling medium therein protects the mucosa and vaginal wall from any heating caused by inefficiencies of the ultrasound element 219. In an invasive procedure, the apparatus may be inserted through an incision or a wound and positioned adjacent to the area to be treated.

After the apparatus has been positioned within the body, the probe 212 and/or the ultrasound element 219 may be further manipulated via angular and/or axial rotation to achieve a desired position relative to the target tissue 282. The ultrasound element 219 may then be rotated and/or translated axially, mechanically or electronically, to provide more thorough coverage of the target tissue, while avoiding damage to the surrounding tissue and structures. As discussed above, in some embodiments of the invention, the probe 212 may rotate relative to the handle 211. Hence, the ultrasonic energy may heat the target tissue to form the lesion 282 while controlling the size and shape thereof. As described above, a deflector (e.g., deflector 270) may be used to control the formation of the lesion(s).

Those skilled in the art will understand that the transducers 221 of any of the above described ultrasound elements 219, 2219 may be operated as a phased array to adjust the depth, shape and/or size of the area of convergence of the ultrasonic energy and that the frequency of the energy delivered by the ultrasound element 219 may be varied depending on the depth of the lesion 282 to achieve a maximum energy delivery to this tissue while minimizing the impact of the energy on surrounding tissue and the tissue surface. Furthermore, the present invention contemplates use with other types of energy, such as, radio frequency, infra-red and x-ray.

Those skilled in the art will understand that changes may be made in details, particularly in matters of shape, size, material and arrangement of parts. Accordingly, various modifications and changes may be made to the embodiments. For example, the type of ultrasound array used may be varied, and the shape of the transducers may be changed. Additional or fewer components may be used, depending on the condition that is being treated using the described apparatus. The specifications and drawings are, therefore, to be regarded in an illustrative rather than a restrictive sense.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. A device for heating target tissue comprising:
   a housing including a tissue contacting surface;
   an array of ultrasound transducers mounted within the housing on an array surface shaped so that ultrasound energy from the transducers converges on a target area a predetermined depth from the tissue contacting surface; and
   a deflector member attached to the housing and extending into a selected field through which the ultrasound energy passes on its way to the target area, the deflector member refracting a selected portion of the ultrasound energy to increase a distance of separation between the array and a proximal edge of a region at which a level of ultrasound energy exceeds a predetermined threshold level relative to an undeflected distance of separation when the deflector member is not attached to the housing.

2. The device according to claim 1, wherein the deflector member extends from a proximal end coupled to the housing to a distal end a predetermined distance from the array surface.

3. The device according to claim 2, wherein a profile of the deflector member in a plane substantially parallel to a plane tangent to a center of the array surface is selected to create a shadow area in which the level of ultrasound energy remains below the predetermined threshold level wherein, if not for the deflector member, the level of ultrasound energy in this shadow area would exceed the predetermined threshold level.

4. The device according to claim 1, wherein a distal end of the deflector member is wider than the proximal end.

5. The device according to claim 4, wherein the deflector member expands gradually outward through a transition area from a central stem to form a substantially conical distal end.

6. The device according to claim 4, wherein the deflector member expands abruptly from a central stem to form a substantially disc-shaped distal end.

7. The device according to claim 1, wherein, the distal end of the deflector member is substantially centrally located within the field through which the ultrasound energy passes on its way to the target area.

8. The device according to claim 7, wherein the array includes a plurality of circular transducers approximately 1 cm in diameter.

9. The device according to claim 1, wherein the transducers are vibrated at a frequency of approximately 2.5 MHz.

10. The device according to claim 9, wherein the array includes at least 10 transducers.

11. The device according to claim 1, wherein the proximal end of the deflector member is removably coupleable to the housing.

12. The device according to claim 1, wherein the transducers and the array surface are fixed with respect to the housing so that the distance of separation between the array and a proximal edge of a region at which a level of ultrasound energy exceeds a predetermined threshold level is varied only through interaction with the deflector member.

13. The device according to claim 12, wherein the deflector member is removable from the housing so that the device may be configured to achieve a first distance of separation between the array and a proximal edge of a region at which a level of ultrasound energy exceeds a predetermined threshold level when the deflector is coupled to the housing and a second distance of separation between the array and a proximal edge of a region at which a level of ultrasound energy exceeds a predetermined threshold level when the member is removed from the housing, the second distance being greater than the first distance.

14. A device for heating target tissue comprising:
   an array of ultrasound transducers mounted within a housing along a shape selected so that ultrasound energy from the transducers converges on a target area a predetermined distance from the array; and
   a deflective shield element selectively mountable over one or more of the transducers to prevent ultrasound energy from the one or more transducers from reaching a particular region to control a distance of separation between the array and a proximal edge of a region at which a level of ultrasound energy exceeds a predetermined threshold level.

15. A device for heating target tissue comprising:
   a housing including a tissue contacting surface;

an array of ultrasound transducers mounted within the housing on an array surface shaped so that ultrasound energy from the transducers converges on a target area a predetermined depth from the tissue contacting surface; and a deflector member selectively attachable to the housing so that, when attached to the housing, the deflector member extends into a field through which the ultrasound energy generated passes on its way to the target area to refract a selected portion of the ultrasound energy selected to increase a distance of separation between the array and a proximal edge of a region at which a level of ultrasound energy exceeds a predetermined threshold level relative to a distance of separation when the deflector member is not attached to the housing.

* * * * *